United States Patent [19]

Vikmon et al.

[11] Patent Number: 5,403,840
[45] Date of Patent: Apr. 4, 1995

[54] INCLUSION COMPLEXES OF N-ETHOXYCARBONYL 1-3-MORPHOLINO-SYDNONIMINE OR SALTS FORMED WITH CYCLODEXTRIN-DERIVATIVES, PREPARATION THEREOF AND PHARMACEUTICAL COMPOSITIONS CONTAINING THE SAME

[75] Inventors: Mária Vikmon; József Szejtli; József Gaál; István Hermecz; Ágnes Horváth, all of Budapest; Katalin Mármarosi, Biatorbágy; Gábor Horváth; Irén Munkácsi, both of Budapest, all of Hungary

[73] Assignee: Chinoin Gyogyszer-Es Vegyeszeti Termekek Gyar Rt., Budapest, Hungary

[21] Appl. No.: 807,852

[22] PCT Filed: Mar. 28, 1991

[86] PCT No.: PCT/HU91/00012
§ 371 Date: Jan. 2, 1992
§ 102(e) Date: Jan. 2, 1992

[87] PCT Pub. No.: WO91/14680
PCT Pub. Date: Oct. 3, 1991

[30] Foreign Application Priority Data

Mar. 28, 1990 [HU] Hungary .............................. 1868/90
Jun. 27, 1990 [HU] Hungary ............. 1868/90/MODIFI

[51] Int. Cl.[6] .................... C07D 271/04; C06B 37/16; A61K 31/41
[52] U.S. Cl. ................................. 514/236.2; 536/46; 544/138; 424/488
[58] Field of Search ........................ 544/138; 536/46; 514/236.2; 424/488

[56] References Cited

U.S. PATENT DOCUMENTS

| | | | |
|---|---|---|---|
| 4,786,507 | 11/1988 | Schmidt | 424/472 |
| 4,834,985 | 5/1989 | Elger et al. | 424/488 |
| 4,869,904 | 6/1989 | Uekama et al. | 424/400 |
| 5,120,546 | 6/1992 | Hansen et al. | 424/444 |
| 5,120,732 | 6/1992 | Schonafinger | 514/236.2 |

FOREIGN PATENT DOCUMENTS 197571  10/1980  European Pat. Off. .

OTHER PUBLICATIONS

Sigma Chemical Co. pp. 1439 & 1550 1994.
Donilova, Dokl. Akad Nauk SSR 303, 1512 (1988).
Merck Index, 11th ed, G143 (1988).

*Primary Examiner*—Robert Gerstl
*Attorney, Agent, or Firm*—Herbert Dubno; Jonathan Myers

[57] ABSTRACT

The invention relates to inclusion complexes of N-ethoxycarbonyl-3-morpholino-sydnonimine or its salts formed with a cyclodextrin derivatives, preparation thereof and pharmaceutical compositions containing the same.

The inclusion complex of N-ethoxycarbonyl-3-morpholino-sydnonimine or its salt formed with cyclodextrin derivative is prepared by a) reacting the N-ethoxycarbonyl-3-morpholino-sydnonimine or its salt and the cyclodextrin derivative in a solvent medium, and if desired recovering the complex from the solution by dehydration, or b) high energy milling of the N-ethoxycarbonyl-3-morpholino-sydnonimine or its salt and the cyclodextrin derivative.

8 Claims, No Drawings

INCLUSION COMPLEXES OF N-ETHOXYCARBONYL 1-3-MORPHOLINO-SYDNONIMINE OR SALTS FORMED WITH CYCLODEXTRIN-DERIVATIVES, PREPARATION THEREOF AND PHARMACEUTICAL COMPOSITIONS CONTAINING THE SAME

CROSS REFERENCE TO RELATED APPLICATIONS

This application is a National Phase of PCT/HU91/00012 filed 28 Mar. 1991 and based upon Hungarian national application 1868/90 filed 28 Mar. 1990 and amended 27 Jun. 1990.

FIELD OF THE INVENTION

The invention relates to the inclusion complexes of N-ethoxycarbonyl-3-morpholino-sydnonimine (Molsidomin) or its salts formed with heptakis-2,6-O-dimethyl-$\beta$-cyclodextrin (Dimeb), hydroxypropyl-$\beta$-cyclodextrin or with $\beta$-or $\gamma$-cyclodextrin, to the preparation thereof and to the pharmaceutical compositions containing the same.

BACKGROUND OF THE INVENTION

Molsidomin is an antianginic and antiischemic compound which is widely used for the prevention and treatment of angina pectoris. Its advantage compared to the organic nitrates is that its effect is more lasting and it has less side-effects, thus it does not become habit forming and it rarely induces headaches which are also less severe. Its antiarrithmic and the fibrinolysis, the blood-platelet aggregation and blood-pressure decreasing effect are distinguished too.

The Molsidomin is on the market in the form of tablets containing 2, 4 (traditional) and 8 mg (delayed-action) of the active ingredient name Corvaton (Casella, Riedel), Morial (Takeda Ltd.). The delayed-action composition contains the active ingredient in a microencapsulated form applying a special wax in a ratio of 1:4, which ensures an effective plasma concentration for 12 hours.

The Molsidomin is relatively fairly soluble in water (18 mg/ml at 25° C.), it is stable at a pH value of 5–7 in water. The rate determining step of the resorption from the stomach and of the intestinal tract is apparently not the solubility. The oral preparation containing 2 mg of the active ingredient is effective for 3–5 hours. The maximal blood level can be achieved within $\frac{1}{2}$–1 hour. It is fairly absorbed along the whole Gi-tract, its bioavailability is satisfactory. Antianginal preparations for preventive purposes are formulated most advantageously with controlled release of the active ingredient. It ensures the extended and controlled resorption of the medicament and the long lasting therapeutically effective plasma level. The side effects can be decreased significantly by the elimination of the too high toxic plasma level. The transdermal formulation with a controlled release of the active agent is especially advantageous.

The resorption of the active ingredient through the skin depends on its physico-chemical properties and lipoid solubility, and mainly on the formulation applied.

Molsidomin itself is resorbed slowly and to a small extent through the skin; its bioavailability is only 4%. For this reason agents enhancing the resorption are used. The European Patent Specification No. 127468 of the Takeda Company describes a percutaneous fairly resorbing Molsidomin preparation, which contains a special penetration enchancer agent of 2 components—a propyleneglycol mixture containing 10% of oleic acid.

The mechanism of the outstanding bioavailability of 95% may be the following: the oleic acid component modifies the permeability of the skin's protective layer (the stratum corneum) by dissolving the barrier lipoid components of the same. Thus the Molsidomin is fairly resorbed through the modified stratum corneum.

It was stated that the resorption of Molsidomin and of propylene-glycol is of similar extent, and of similar quantity respectively, which means, that only the Molsidomin dissolved in the propylene-glycol will be resorbed.

DESCRIPTION OF THE INVENTION

It has been found, that the effect of Molsidomin or its salts can be retarded by complexation with heptakis-2,6-O-dimethyl-$\beta$-cyclodextrin, hydroxypropyl-$\beta$-cyclodextrin, or with $\beta$-cyclodextrin or $\gamma$-cyclodextrin.

The present invention relates to the inclusion complexes of N-ethoxycarbonyl-3-morpholino-sydnonimine or its salts formed with heptakis-2,6-O-dimethyl-$\beta$-cyclodextrin, hydroxypropyl-$\beta$-cyclodextrin or with $\beta$-or $\gamma$-cyclodextrin. The inclusion complexes according to the invention contain 1–40 moles, advantageously 2–4 moles, of the above cyclodextrin derivatives related to 1 mole of N-ethoxycarbonyl-3-morpholino-sydnonimin.

The inclusion complexes according to the invention can be prepared by reacting N-ethoxycarbonyl-3-morpholino-sydnonimin or its salts are reacted in a solvent with the selected cyclodextrin derivative and if desired the complex is recovered from the solution by dehydration.

As solvent water and/or with water miscible organic solvents, e.g. $C_{1-3}$ alkanols, advantageously ethyl alcohol are used. The complexes according to the invention can be recovered from the solution by lyophilization, by vacuum drying. The complexes according to the invention may be prepared also by high energy milling of the components as described or referred to in Hungarian patent specification T 52366. The complexes of the invention can be used in therapy, e.g. in the form of tablets, pellets, microcapsules, ointments, injections, drops, infusions preferably in the form of one a day tablets or microcapsules. Doses of the inclusion complexes of this invention may vary with the age, body weight and conditions of the subject, the administration route, the number of administrations or the like, but is in the range of 6 to 800 mg per day, preferably 10 to 400 mg per day.

The delayed action effect prevails particularly in the use the pharmaceutical composition in the form of one-a day tablets, microcapsules and ointments exceedingly suitable for percutaneous use, respectively. The pharmaceutical compositions of the invention are prepared in a customary manner. The adjuvants and carriers are those which are usually used in the field of pharmaceutical preparations.

Complex interaction in solution can be illustrated by the membrane permeation test. Visking-type cellophane membrane (average pore diameter 24 angstroms) was used. Aqueous solutions of Molsidomin at a concentration of 1 and 2 mg/ml were put in the donor cell, while distilled water was placed in the receptor compartment of the membrane permeation cell apparatus. The solutions were stirred by magnetic stirrers and were kept at 37+1° C. At appropriate time intervals samples were pipetted from the receptor solutions and concentration of Molsidomin permeated from the donor cell was measured by UV-spectrophotometry. The test was repeated in the presence of different cyclodextrins at different concentrations in the donor cell compartment.

The time required for the diffusion of 50% Molsidomin (T 50%) is listed in Table 1.

TABLE 1

Diffusion half life (T 50%) of Molsidomin in the presence of cyclodextrins

|  | T 50% (hours) |
|---|---|
| Molsidomin alone | 1.0 |
| +$\beta$CD 20 mg/ml | 1.5 |
| +DIMEB | |
| 25 mg/ml | 1.3 |
| 50 mg/ml | 1.8 |
| 100 mg/ml | 2.4 |
| +HP$\beta$CD | |
| 50 mg/ml | 1.5 |
| 100 mg/ml | 2.0 |

The permeation rate of Molsidomin can be significantly decreased which points to a considerable interaction between Molsidomin and the examined cyclodextrins. Only the free (uncomplexed) drug can permeate freely across the applied membrane. The concentration of the free drug is depending upon the value of the complex stability constant. The smaller the stability constant the greater is the free drug concentration available for permeation. On the contrary if the complex is very stable or the cyclodextrin concentration is sufficiently high (is present in high excess) the complex dissociation equilibrium is shifted towards the complexation, and the diffusion is considerably hindered. The obtained results provide a principle for controlling (sustaining, modifying) the release profile of Molsidomin across a semipermeable membrane forming polymer by means of cyclodextrin complexation according to the invention.

The invention is illustrated by the following examples, without restricting the invention to them.

EXAMPLES

1. Molsidomin-Dimeb complex prepared by lyophilization 7 g of Dimeb (5 mmoles, moisture content 2%) are dissolved in 100 ml of distilled water, thereafter 0.4 g of Molsidomin are dissolved in the solution obtained. The homogenous solution obtained is frozen and subjected to dehydration by lyophilization, taking care that in the course of working processes the solution should be exposed to the slightest possible light effect. It is expedient to wrap up the vessel while dissolving in a black paper. The product obtained is a light, loose powder, its active ingredient content determined spectrophotometrically is 5±0,4%. It corresponds to a molar ratio of about 1:3 Molsidomin-Dimeb.

Test proving the fact of complex formation

Differential Scanning Calorimetric (DSC) curves showed characteristic differences between the physical mixture and the liophylized complex with DIMEB. The DSC curves of the mechanical mixture and of the complex run differently, in case of the mixture a sharp endothermic peak at 140°–142° C. indicated the melting of Molsidomin, while the curve of the complex shows at this temperature range a sharp exothermic peak. This latter can be explained by the heat induced chemical decomposition of the complex.

X-ray diffractometry

X-ray diffraction pattern of the complex revealed an amorphous structure of the complex, though both of the starting species are crystalline. Therefore a new type solid state structure can be a result of inclusion complex formation.

$^{13}$C NMR studies proved that the ethoxycarbonyl part of the Molsidomin molecule is located inside the cavity of DIMEB. This is illustrated by chemical shifts ($\Delta\delta$), because the degree of chemical shifts indicates the mode of inclusion in solution. The most pronounced values refer to the part of the guest molecule which is included in the cyclodextrin cavity. $\Delta\delta = -2.2 - +1.3$ ppm can be measured concerning the ethoxycarbonyl part while practically no chemical shifts can be measured on the morpholino part of the guest molecule.

2. Preparation of the Molsidomin-Dimeb complex by spray-drying 14 g of Dimeb (10 mmoles, moisture content 2%) and 1.2 g of Molsidomin (5 mmoles) are dissolved in 180 ml of distilled water by ultrasonication. The obtained homogenous solution is spray-dryed, temperature of the input air is 125° C. and that of the output air is 92° C. While processing the solution, and the vessel containing the product, respectively is protected from light and continuously stirred. Yield 10 g.

The product obtained is a loose white powder, their active ingredient content is about 7.8±0.2% determined by a spectrophotometric method, it corresponds to a molar ratio of about 1:2. The thermoanalytical curves (DSC) of the spray-dried product and the Rtg. diffraction powder diagram of the same are identical with that of the complex prepared by lyophilization.

3. Preparation of Molsidomin-$\beta$-CD complex by kneading 6.6 g of $\beta$-cyclodextrin (5 mmoles, content 14%) and 0.6 g (2.5 mmoles) of Molsidomin are homogenized in a friction mortar protected from light if possible. 3 ml of a 50% ethyl alcohol are added and the dense suspension is stirred for further 30 minutes after spreading the product of hard lubricity and paste like consistence on a watch-glass, it is dried to constant weight in the presence of phosphoruspentoxide in an exsiccator. The product obtained is pulverized, its active ingredient content is 9±0.5% determined by the spectrophotometric method, which corresponds to a molar ratio of about 1:2. DSC curves of Molsidomin, its mechanical mixture and its complex with $\beta$-CD are significantly different. The endothermic peak at 140°–142° C. on the DSC curve completely disappeared in the case of complexes with $\beta$-CD prepared by both kneading or liophylization. It indicates that the Molsidomin is complexed, and at 130°–160° C. temperature range not even a 50 fold magnified curve showed endothermic peak of melting in the case of complex prepared by lyophilization.

Taking the DSC curve in argon atmosphere the decomposition of Molsidomin is markedly inhibited upon heating, which enables quantitation of free and complexed amount of Molsidomin, based upon the comparation of the melting peak areas.

The melting of pure Molsidomin is releated to an enthalphy change of $\Delta H = 140$ mJ/mg.

The entire amount of Molsidomin proved to be complexed in the case of freeze dried complex and less than 10% of the Molsidomin content is absorbed in complex prepared by kneading.

4. Preparation of Molsidomin HP-β-CD complex by lyophilization 13 g HP-β-CD (0.01 mole) (DS=2.7 DS means the average substitution degree per cyclodextrin molecule) are dissolved in 100 ml of distilled water. 0.7 g of Molsidomin are added and the dissolution is promoted by stirring, the solution is protected from light. The homogenous solution obtained is dehydrated by methods as in former examples. The product is a loose white powder, its Molsidomin content is 5±0.2% by the spectrophotometric method, which corresponds to a molar ratio of about 1:3 Molsidomin: HP-β-CD.

5. Preparation of Molsidomin-β-CD complex granule by kneading 1 g (4.1 mmol) of Molsidomin and 11 g of β-CD (8.3 mmol moisture content 14%) are mixed in a mortar, 4 ml of 30% ethyl alcohol are added, the dense suspension is kneaded for 30 minutes. The obtained product of paste like consistence was spread on a tray and dried at 40° C. for two hours. Thereafter the semidried product was rubbed through a sieve of pore size 1 mm. The obtained granule was dried at 60° C. to constant weight and screened repeatedly through a sieve obtaining grains of the desired size. Active ingredient content 10±0.5% determined by UV-spectrophotometry, corresponding approximately to 1:2 molar ratio of Molsidomin,: β-CD.

The obtained granule has appropriate flowing properties with low powder fraction and is applicable to make a tablet core containing the medicament in the desired dose by direct compression, or preparing sustained release formulation by direct compression with known matrix forming polymer components, or applying the fluidization technique for preparing film coated pellets, where the coating acts as a semipermeable membrane during the dissolution process. The table core obtained by the simplest direct compression technology is applicable for preparing controlled sustained release dosage froms by coating them with polymer or a blend of polymers known in the art.

Membrane permeation test

Dialysis profile of Molsidomin-β-CD granule was examined using the same permeation cell as described above.

Molsidomin at a concentration of 1 mg/ml and equivalent amount of complex granule were used in the experiment The measurable Molsidomin concentrations in the receptor cell at different time intervals are listed in Table 2.

TABLE 2

Concentration of Molsidomin in the receptor cell.

| Time (hours) | concentration (mg/ml) | |
|---|---|---|
| | Molsidomin alone | Molsidomin-β-CD granule |
| 1 | 0.20 | 0.16 |
| 2 | 0.29 | 0.24 |
| 3 | 0.32 | 0.27 |
| 4 | 0.34 | 0.31 |

100% diffusion corresponding to 0.33 mg/ml Molsidomin concentration in the receptor cell.

6. Molsidomin tablet of 2 mg active ingredient content per tablet

Composition:
40 mg of Molsidomin-Dimeb complex with a 5% active ingredient content, prepared according to example 1.
40 mg of maize starch
78 mg of milk sugar
2 mg of magnesium stearate
Total weight of the tablet: 160 mg 7. Preparation of ointment for percutaneous use containing 10 mg of Molsidomin as active agent and 2 g of gel Molsidomin-Dimeb complex (active ingredient content 5%) 2 g are dissolved in 20 ml of distilled water. To the solution 50 mg of KLUCEL-HF (hydroxy-propyl-cellulose) are added while vigorous stirring. A viscous solution hardly to stir is obtained which is let to stand for 1 day at room temperature, protected from light. Thus a transparent ointment is formed, 2 g of which contains 10 mg of Molsidomin.

8. Non sustained release formulations

| a.) | | | | | | |
|---|---|---|---|---|---|---|
| Molsidomin-β-CD-complex (contains 1 to 15% Molsidomin) | 100 mg | 50 | 150 | 300 | 200 | 250 |
| Sodium starch glycolate | 10 mg | 10 | 15 | 20 | 20 | 20 |
| Saccharose | 90 mg | 125 | 133 | 140 | 13 | 145 |
| Maize starch | 5 mg | 5 | 7 | 12 | 10 | 12 |
| Glucose | 14 mg | 29 | 20 | 14 | 21 | 23 |
| Silicon dioxide | 8 mg | 8 | 12 | 10 | 10 | 11 |
| Magnesium stearate | 3 mg | 3 | 3 | 4 | 4 | 4 |
| For one tablet: TOTAL = | 230 mg | 230 | 340 | 500 | 400 | 465 |
| b.) | | | | | | |
| Molsidomin-β-CD-complex (contains 1 to 15% Molsidomin) | 50 mg | 100 | 150 | 200 | 250 | 300 |
| Silicon dioxide | 0, 1 | 0, 2 | 0, 3 | 0, 4 | 0, 4 | 0, 5 |
| Ethylcellulose 20 cps | 1, 5 | 3 | 4 | 5 | 5 | 5 |
| Maize starch | 45 | 60 | 65 | 70 | 70 | 70 |
| Magnesium stearate | 1 | 2 | 3 | 4 | 4 | 5 |
| Polyvidone | 4 | 6 | 7 | 8 | 8 | 8 |
| Talc | 3 | 5 | 7 | 8 | 8 | 8 |
| Lactose | 125, 4 | 123, 8 | 133, 7 | 104, 6 | 104, 6 | 103, 5 |
| For one tablet: TOTAL = | 230 mg | 300 | 370 | 400 | 450 | 500 |

| -continued | | | | | | |
|---|---|---|---|---|---|---|
| c.) | | | | | | |
| Molsidomine-β-CD-complex (contains 1 to 15% Molsidomin) | 50 mg | 100 | 150 | 200 | 250 | 300 |
| Lactose | 25 mg | 30 | 35 | 35 | 35 | 30 |
| Polyvidone | 10 mg | 12 | 15 | 15 | 15 | 15 |
| Maize starch | 37 mg | 50 | 50 | 50 | 50 | 50 |
| Talc | 10 mg | 12 | 12 | 15 | 15 | 15 |
| Magnesium stearate | 3 mg | 4 | 4 | 4 | 5 | 5 |
| Saccharose | 166 mg | 112 | 114 | 101 | 90 | 85 |
| For one tablet: TOTAL = | 300 mg | 320 | 380 | 420 | 460 | 500 |
| d.) | | | | | | |
| Molsidomin-β-CD-complex (contains 1 to 15% Molsidomin) | 50 mg | 100 | 150 | 200 | 250 | 300 |
| Lacca depurata | 8 mg | 10 | 12 | 14 | 15 | 15 |
| Saccharose | 127 mg | 111 | 103 | 93 | 85 | 80 |
| Maize starch | 40 mg | 50 | 50 | 50 | 50 | 50 |
| Talc | 3 mg | 4 | 5 | 8 | 10 | 10 |
| Polyvidonum | 22 mg | 25 | 30 | 35 | 40 | 45 |
| For one tablet: TOTAL = | 250 mg | 300 | 350 | 400 | 450 | 500 |
| e.) | | | | | | |
| Molsidomin-β-CD-complex (contains 1 to 15% Molsidomin) | 50 mg | 100 | 150 | 200 | 250 | |
| Mannitol | 160 mg | 129 | 105, 5 | 102 | 92 | |
| Maize starch | 92 mg | 80 | 70 | 70 | 60 | |
| Lactose | 50 mg | 60 | 70 | 70 | 80 | |
| Hypromellose | 4 mg | 6 | 8 | 10 | 10 | |
| Magnesium stearate | 2, 5 mg | 3 | 3, 5 | 4 | 4 | |
| Silicium dioxyde | 1, 5 mg | 2 | 3 | 4 | 4 | |
| For one tablet: TOTAL = | 360 mg | 380 | 410 | 460 | 500 | |
| f.) | | | | | | |
| Molsidomin-β-CD-complex (contains 1 to 15% Molsidomin) | 50 mg | 100 | 150 | 200 | | |
| Lactose anhydrous | 225 mg | 187 | 186 | 176 | | |
| Cellulose microcrystalline | 72 mg | 90 | 100 | 120 | | |
| Magnesium stearate | 3 mg | 3 | 4 | 4 | | |
| For one tablet: TOTAL = | 350 mg | 380 | 440 | 500 | | |

9. Sustained release formulation

| a.) | | | | | |
|---|---|---|---|---|---|
| Molsidomin-β-CD-complex (contains 1 to 15% Molsidomin) | 150 mg | 200 | 250 | 300 | 350 |
| Saccharose | 41 mg | 55 | 68 | 82 | 95 |
| Maize Starch | 13 mg | 17 | 22 | 26 | 31 |
| Polyvidone | 6 mg | 8 | 10 | 12 | 14 |
| For microencapsulated preparation: | 210 mg | 280 | 350 | 420 | 490 |
| b.) | | | | | |
| Molsidomin-β-CD-complex (contains 1 to 15% Molsidomin) | 150 mg | 200 | 250 | 300 | |
| 15000 carboxymethylcellulose | 115 mg | 156 | 150 | 130 | |
| Lactose 1 H$_2$O | 62 mg | 60 | 56 | 65 | |
| Magnesium stearate | 3 mg | 4 | 4 | 5 | |
| For one tablet: TOTAL = | 330 mg | 420 | 460 | 500 | |
| c.) | | | | | |
| Molsidomin-β-CD-complex (contains 1 to 15% Molsidomin) | 50 mg | 200 | 250 | | |
| Carnauba wax | 215 mg | 220 | 245 | | |
| Stearylic acid | 66 mg | 82 | 100 | | |
| Magnesium stearate | 2 mg | 3 | 3 | | |
| For one table: TOTAL = | 333 mg | 405 | 500 | | |
| d.) | | | | | |
| Molsidomin-β-CD-complex (contains 1 to 15% Molsidomin) | 150 mg | 200 | 250 | | |
| P.V.C. | 111 mg | 120 | 122 | | |
| P.V.A. | 111 mg | 120 | 122 | | |
| Magnesium stearate | 3 mg | 5 | 6 | | |
| For one tablet: TOTAL = | 375 mg | 445 | 500 | | |
| e.) | | | | | |
| Molsidomin-β-CD-complex (contains 1 to 15% Molsidomin) | 150 mg | | | | |
| Ethylcellulose 300 mPa.s. | 300 mg | | | | |
| Ethylcellulose 30 mPa.s. | 48 mg | | | | |
| Magnesium stearate | 2 mg | | | | |
| For one tablet: TOTAL = | 500 mg | | | | |
| f.) | | | | | |
| Molsidomin-β-CD-complex (contains 1 to 15% Molsidomin) | 150 mg | 200 | 250 | 300 | 350 |

| | -continued | | | | |
|---|---|---|---|---|---|
| Calcium diphosphate | 39 mg | 52 | 66 | 78 | 80 |
| Eudragit Ne 40D | 34 mg | 45 | 57 | 68 | 70 |
| Magnesium stearate | 3 mg | 4 | 5 | 5 | 6 |
| Talc | 4 mg | 5 | 7 | 9 | 9 |
| For one tablet: TOTAL = | 230 mg | 316 | 385 | 460 | 515 |

What we claim is:

1. Inclusion complex of N-ethoxycarbonyl-3-morpholino-sydnonimine or its salt formed with a cyclodextrin derivative, in a molar ratio of 1:1 to 1:40.

2. Inclusion complex defined in claim 1 of N-ethoxycarbonyl-3-morpholino-sydnonimine or its salt formed with a heptakis-2,6-O-dimethyl-62-cyclodextrin.

3. Inclusion complex according to claim 1, containing 2-4 moles of heptakis-2,6-O-dimethyl-$\beta$-cyclodextrin related to 1 mole of N-ethoxycarbonyl-3-morpholino-sydnonimine.

4. Inclusion complex defined in claim 1 of N-ethoxycarbonyl-3-morpholino-sydnonimine or its salt formed with hydroxypropyl-$\beta$-cyclodextrin.

5. Inclusion complex defined in claim 1 of N-ethoxycarbonyl-3-morpholino-sydnonimine or its salt formed with $\beta$-or $\gamma$-cyclodextrin.

6. Pharmaceutical composition consisting essentially of as active ingredient an effective amount of the inclusion complex of N-ethoxycarbonyl-3-morpholino-sydnonimine or its salt formed with heptakis-2,6-O-dimethyl-$\beta$-cyclodextrin or with hydroxypropyl-$\beta$-cyclodextrin or $\beta$- or $\gamma$-cyclodextrin in a molar ratio of 1:1 to 1:40 and customary pharmaceutical filling, diluting and further auxiliary materials.

7. Pharmaceutical composition according to claim 6, characterized by, that it is formulated in the form of one-a day tablet or a microcapsule.

8. Method of treatment of anginic and ischemic diseases in humans which comprises administering to the human an effective amount of an inclusion complex of N-ethoxycarbonyl-3-morpholino-sydnonimine or its salt formed with a cyclodextrin derivative as defined in claim 1.

* * * * *